(12) United States Patent
Seifer et al.

(10) Patent No.: US 7,378,388 B2
(45) Date of Patent: May 27, 2008

(54) METHOD OF UTILIZING NEUROTROPHINS TO MANIPULATE REPRODUCTIVE CAPACITY

(75) Inventors: David B. Seifer, Holmdel, NJ (US); Robert Shelden, Kendall Park, NJ (US); Bo Feng, Edison, NJ (US); Cheryl Dreyfus, Short Hills, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 196 days.

(21) Appl. No.: 11/243,619

(22) Filed: Oct. 5, 2005

(65) Prior Publication Data

US 2006/0088884 A1 Apr. 27, 2006

Related U.S. Application Data

(62) Division of application No. 10/209,779, filed on Jul. 31, 2002, now Pat. No. 7,097,984.

(60) Provisional application No. 60/309,061, filed on Jul. 31, 2001.

(51) Int. Cl.
*A01N 37/00* (2006.01)
*A61K 38/00* (2006.01)

(52) U.S. Cl. .................... 514/2; 514/7; 514/8; 514/12

(58) Field of Classification Search .................... None
See application file for complete search history.

(56) References Cited

FOREIGN PATENT DOCUMENTS

| JP | 0 958 831 | * | 11/1999 |
|---|---|---|---|
| WO | WO 93/25684 A1 | | 12/1993 |

OTHER PUBLICATIONS

Fedorushchenko et al. Russian Journal of Developmental Biology. 30; 1999: 395-397.*
Website at glaucoma.org/learn/glaucoma_facts.html, downloaded Sep. 6, 2007; pp 1-3.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Nebreda, et al. Induction by NGF of Meiotic Maturation of Xenopus Oocytes Expressing the trk Proto-Oncogene Product. Science. Apr. 26, 1991. vol. 252, No. 5005, pp. 558-561.
Anderson et al., "Neurotropins and Their Receptors Are Expressed in the Human Fetal Ovary," J. Clin. Endocrinol. Metab., vol. 87, No. 2 (2002) pp. 890-897.

Conover et al., "Neuronal deficits, not involving motor neurons, in mice lacking BDNF and/or NT4," Nature, vol. 375, (May 18, 1995) pp. 235-238.
Dissen et al, "Direct effects of nerve growth factor on thecal cells from antral ovarian follicles," Endrocrinology, vol. 141, No. 12 (2000) pp. 4736-4750.
Dissen et al., "Expression of neurotrophins and their receptors in the mammalian ovary is developmentally regulated: changes at the time of folliculogenesis," Endocrinology, vol. 136, No. 10 (1995) pp. 4681-4692.
Dissen et al., "Participation of nerve growth factor in the regulation of ovarian function," Zygote, vol. 4, (Nov. 1998) pp. 309-312.
Dissen et al., "A role for *Trk*A nerve growth factor receptors in mammalian ovulation," Endocrinology, vol. 137, No. 1, (1996) pp. 198-209.
Giudice et al., "Growth Factors in Normal Ovarian Follicle Development," Semin. Reprod. Endocrinol., vol. 14, No. 3 (Aug. 1996) pp. 179-196.
Lara et al., "The gene encoding nerve growth factor is expressed in the immature rat ovary: effect of denervation and hon-nonal treatment," Endocrinology, vol. 126, No. 1 (1990) pp. 357-363.
Lara et al., "Involvement of nerve growth in female sexual development," Endocrinology, vol. 126, No. 1 (1990) pp. 364-375.
Mayerhofer et al., "Involvement of nerve growth factor in the ovulatory cascade: *trk*A receptor activation inhibits gap junctional communication between thecal cells," Endocrinology, vol. 137, No. 12 (1996) pp. 5662-5670.
Mischel et al., "The extracellular domain of p75$^{NTR}$ is necessary to inhibit neurotrophin-3 signaling through TrkA," J. Biol. Chem., vol. 276, No. 14 (Apr. 6, 2001) pp. 11294-11301.
Ojeda et al., "Neurotrophic and cell—cell dependent control of early follicular development," Mol Cell Endo., vol. 163, (2000) pp. 67-71.
Parvinen et al., "Expression of β-nerve growth factor and its receptor in rat seminiferous epithelium: specific function at the onset of melosis," J. Cell. Biol., vol. 117, (1992) pp. 629-641.
Promega Technical Bulletin #257, "BDNF $E_{max}$™ ImmunoAssay System," Madison, WI, Revised (Jan. 1998).
Reichardt et al., "in Molecular Approaches to Neuronal Development," Cowan et al., eds., Oxford University Press, New York, (1997) pp. 220-263.
Schneyer et al., "Dynamic changes in the intrafollicular inhibin/activin/follistatin axis during human follicular development: relationship to circulating hormone concentrations," J. Clin. Endocrinol. Metab., vol. 85, No. 9 (2000) pp. 3319-3330.
Seidl et al., "Expression of nerve growth factor and neurotrophin receptors in testicular cells suggest novel roles for neurotrophins outside the nervous system," Reprod. Fert. Dev., vol. 8, (1996) pp. 1075-1087.

(Continued)

*Primary Examiner*—Elizabeth C. Kemmerer
*Assistant Examiner*—Christina Borgeest
(74) *Attorney, Agent, or Firm*—Licata & Tyrrell PC

(57) ABSTRACT

Methods and kits are provided for manipulating and predicting the reproductive capacity of a female subject. The presence of endogenous neurotrophins and addition of exogenous neurotrophins, particularly BDNF, NT-4/5, and NGF, increase the reproductive capacity of a female patient by binding to receptors on the oocytes and stimulating maturation of the oocytes. Administration of antagonists act as a contraceptive because the antagonists prevent the neurotrophins from binding to oocyte receptors. Neurotrophins may also be used to stimulate the maturation of oocyte in vitro.

6 Claims, 6 Drawing Sheets

OTHER PUBLICATIONS

Seifer et al., "Brain-derived neurotrophic factor (BDNF): A noval human ovarian follicular protein," J. Clin. Endocrinol. Metab., vol. 87, No. 2 (2002) pp. 655-659.

Seifer et al., "Differential secretion of dimeric inhibin in cultured luteinized granulosa cells as a function of ovarian reserve," J. Clin. Endocrinol. Metab., vol. 81, (1996) pp. 736-739.

Shibayama et al., "Cellular localization of the Trk neurotrophin receptor family in human non-neuronal tissues," Am. J. Pathol., vol. 248, No. 6 (1996) pp. 1807-1818.

Sommerfeld et al., "Down regulation of the neurotrophin receptor TrkB following ligand binding," J. Biol. Chem., vol. 275, No. 12 (Mar. 24, 2000) pp. 8982-8990.

Tessarollo, "Peiotropic functions of neurotrophins in development," Cytokine and Growth Factor Reviews, vol. 9, No. 2 (1998) pp. 125-137.

Vesa et al., "p75 Reduces TrkB tyrosine autophosphorylation in response to brain-derived neurotrophic factor and neurotrophin 4/5," J. Biol. Chem., vol. 275, No. 32 (Aug. 11, 2000) pp. 24414-24420.

Waraksa et al., "Neurotrophin-3 augments steroid secretion by hamster ovarian follicles *in vitro*," Zoolog Sci., vol. 12, (1995) pp. 499-502.

Yamamoto et al., "Expression of mRNAs for neurotrophic factors (NGF, BDNF, NT-3 and CDNF) and their receptors ($p^{75NGFR}$, Trk A, Trk B and Trk C) in the adult human peripheral nervous system and nonneural tissues," Neurochemical Research, vol. 21, No. 8 (1995) pp. 929-938.

Zaccaro et al., "p75 co-receptors regulate ligand-dependent and ligand-independent Trk receptor activation, in part by altering Trk docking subdomains," J. Biol. Chem., vol. 276, No. 33 (Agu. 17, 2001) pp. 31023-31029.

* cited by examiner

METHOD OF UTILIZING NEUROTROPHINS TO MANIPULATE REPRODUCTIVE CAPACITY

CROSS-REFERENCE TO RELATED APPLICATIONS

The present utility patent application is a divisional of U.S. Ser. No. 10/209,779 filed Jul. 31, 2002 now U.S. Pat. No. 7,097,984 which claims priority to provisional patent application entitled "Brain Derived Neurotrophic Factor A Marker of Reproductive Potential in Women," U.S. Ser. No. 60/309,061 (Seifer et al.), filed Jul. 31, 2001, the disclosure each of which are incorporated by reference in their entireties herein.

GOVERNMENT INTEREST

A portion of this work was funded by the National Institutes of Health under grant 5 numbers AG15425, HD23315 and NS36647. The government may own certain rights in the present invention.

FIELD OF THE INVENTION

The present invention relates to the field of reproductive endocrinology, molecular biology, and the regulation reproductive factors in female subjects. In particular, this invention provides novel methods for manipulating fertility in female subjects using neurotrophins to influence oocyte maturation.

BACKGROUND OF THE INVENTION

Various publications or patents are referred to throughout this application or at the end of this specification to describe the state of the art to which the invention pertains. Each of these publications or patents is incorporated by reference herein. Complete citations of scientific publications are set forth at the end of the specification.

An individual's reproductive choices are among the most serious and personal choices made in a lifetime. It is important to be able to control fertility so that an individual is able to conceive when desired, but also to prevent pregnancy at all other times. Both infertility and unwanted pregnancy can have grave economic, emotional, and psychological impacts.

Infertility affects about 5.3 million people in the United States alone and is a disease of the reproductive system that impairs the body's ability to perform the basic function of reproduction. Infertility, defined as the inability to conceive after one year of unprotected intercourse, can be attributed to the male, the female, or sometimes both parties. Women tend to be most fertile in their early 20s and fertility declines rather slowly until about age 35, after which it declines rapidly. If women turn to in vitro fertilization (IVF) to aid the conception process, the treatment is expensive and only has about a 30% success rate with the current state of the art. Contraception is another key reproductive choice that is the foundation of a multi-billion dollar industry. Any improvement in the arts of treatment of infertility and providing contraception would be significant.

When focusing particularly on the female role in reproduction, one key factor in female fertility is the oocyte itself. The process of oocyte maturation and follicle development is a complex and carefully orchestrated phenomenon, involving gonadotropin hormones and a rapidly expanding list of other intraovarian regulators. (Giudice, et al. (1996)). These regulators include growth factors belonging to the insulin-like growth factor family and the transforming growth factor-beta family. Examples of other known intraovarian regulators include cytokines and factors influencing angiogenesis, such as vascular endothelial growth factor.

Neurotrophins are a family of soluble polypeptide growth factors widely recognized for their roles in the mammalian nervous system. They include nerve growth factor (NGF), brain-derived neurotrophic factor (BDNF), neurotrophin-4/5 (NT-4/5) and neurotrophin-3 (NT-3) Although originally described in the nervous system, many members of the neurotrophin family are expressed in a variety of non-neuronal tissues including the cardiovascular, immune, endocrine and reproductive systems. (Tessarollo (1998) and Yamamoto, et. al (1996)). Several members of the neurotrophin family (NGF, BDNF, NT-4/5, NT-3) and their respective receptor tissue tyrosine kinases (Trk A for NGF, Trk B for BDNF and NT-4/5 and Trk C for NT-3) have been found to be expressed in the mammalian ovary. (Dissen, et. al (1996)). Researchers initially thought the action of neurotrophins within the rodent ovary was limited to their support of ovarian innervation. However, in recent years some of these neurotrophins and their respective receptors have been found to influence rodent ovarian function including ovulation (Mayerhoffer, et al. (1996)), steroid secretion (Waraksa, et al. (1995)) and follicular development (Lara, et al. (1990) *Endocrinology*. 126: 357-363 and 364-375, Dissen et al. (1995), and Ojeda, et al. (2000)). In the testis, neurotrophins and their receptors have been clearly associated with spermatogenesis, demonstrating distinct distributions between somatic and germ cells. (Vesa, et al. (2000) and Seidl, et al. (1996)). Nerve growth factor activation of Trk A in cultured thecal cells is involved in disruption of gap junctions (Mayerhoffer, et al. (1996)) and may stimulate cyclooxygenase II production, progesterone secretion and cell proliferation (Parvinen, et al. (1992)), events associated with ovulation. Until now, there has been no description in the art of using neurotrophins to manipulate the reproductive capacity of female subjects. With the impact for both individuals making personal reproductive choices, the doctors who treat the individuals, and the drug companies that manufacture pharmaceuticals, it would be a significant improvement in the art if neurotrophins could be utilized to manipulate fertility and as a diagnostic for reproductive capacity in female subjects. Any invention that can decrease the cost and reduce the emotional strain related to controlling fertility would be highly useful in the art.

SUMMARY OF THE INVENTION

A first aspect of the present invention is to treat infertility in vivo using one or more members of the neurotrophin family to stimulate oocyte production and maturation, including neurotrophin action in paracrine and autocrine signaling pathways, which ultimately leads to increased fertility in female subjects.

A second aspect of the present invention is to improve the quality and fertility of oocytes.

A third aspect of the present invention is the use of cAMP and signal transduction factors, particularly forskolin, either alone or in combination to stimulate oocyte maturation.

Another aspect of the present invention includes the method of using neurotrophins to test female reproductive capability by determining the average number of receptors for a given neurotrophin on a sample of oocytes from a subject. Preferably, the receptor of interest is Trk B or Trk A.

A neurotrophin that binds to the receptor of interest is added to a sample of at least one oocyte from a female subject and then the amount of bound neurotrophin to the surface the oocytes is tested.

A related embodiment contemplates testing female reproductive capability by adding a neurotrophin to a sample of at least one oocyte from a female subject, then adding monoclonal antibodies that selectively bind to the neurotrophin. The quantity of bound monoclonal antibodies is then determined and used to calculate the average number of receptors per oocyte, indicating the average capacity to bind neurotrophins for the oocytes of that subject. Kits for carrying out both variations of the method are also provided. The reproductive capacity of a subject positively correlates to the amount of neurotrophin per oocyte bound in the sample. Likewise, the reproductive capacity of a subject positively correlates to the quantity of bound monoclonal antibody per oocyte in the sample.

Another teaching of the invention is screening Trk receptors on the surface of oocytes for genetic abnormalities, such as point mutations and gene rearrangements. A kit for carrying out this method is also provided.

The present invention may also be embodied in a method and kit for measuring one or more endogenous neurotrophin levels in a female subject as a prognosticator of reproductive capacity.

Methods of using antagonists to block the receptor sites for neurotrophins on oocytes and act as a contraceptive are also elucidated.

BRIEF DESCRIPTION OF THE DRAWINGS

The invention is best understood from the following detailed description when read in connection with the accompanying drawings, in which.

DETAILED DESCRIPTION OF THE INVENTION

DEFINITIONS

Figure 1:
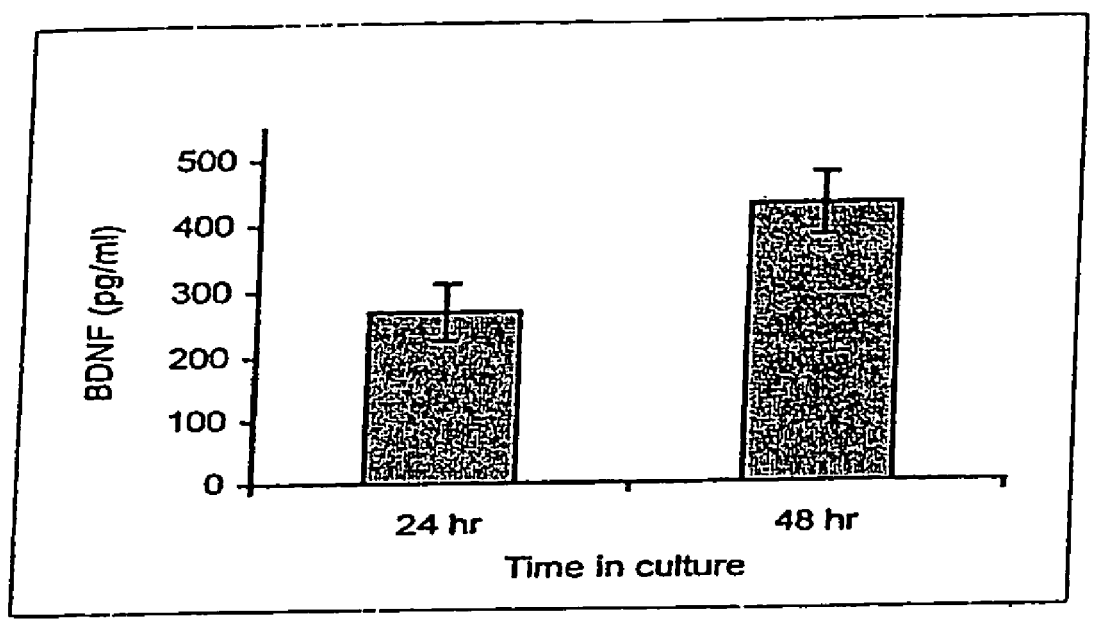
FIG. 1. BDNF production and secretion by cumulus cells. Cumulus cells were collected from individual subjects (n=18) and were plated at $1.5 \times 10^5$ cells in 0.3 ml medium in 24-well plates. Culture medium was collected at 24 h and 48 h. Graph was plotted using mean±standard error [SE]. *p=0.01.

Various terms relating to the present invention are used throughout the specification and claims.

As used herein, "neurotrophin" refers to a neurotrophin, including NGF, NT-3, NT-4/5, and BDNF, from any species, including murine, bovine, ovine, porcine, equine, avian, and preferably human, in native sequence or in a genetically engineered form, and from any source, whether natural, synthetic, or recombinantly produced.

"Signal transduction agent" is a molecule that mediates the action of cAMP leading to the eventual release of an effector agent.

The term "parenteral" refers to introduction of the polypeptide by intravenous, intraarterial, intraperitoneal, intramuscular, intraventricular, intracranial, subcutaneous, subdermal, oral, nasal, or rectal routes.

"Therapeutically effective dose" is a dose that produces the effects for which it is administered.

"Autocrine" is a form of signaling in which secretion of a substance stimulates the secretory cell itself "Paracrine" is a form of signaling in which the target cell is close to the signal-releasing cell.

As used herein, the term "oocytes" refers to the gamete from the follicle of a female animal.

"Immature oocytes" are oocytes that are viable but incapable of fertilization without additional growth or maturation.

"Polar body extrusion" is the process by which the polar body is created and split from the primary and secondary oocyte during meiosis.

"Antibodies" as used herein includes polyclonal and monoclonal antibodies, chimeric, single chain, and humanized antibodies, as well as Fab fragments, including the products of a Fab or other immunoglobulin expression library.

The term "specific binding affinity" means that the antibody or antibody fragment binds to target compounds (i.e., neurotrophins, such as BDNF) with greater affinity than it binds to other compounds under specified conditions. Antibodies or antibody fragments having specific binding affinity to a compound maybe used to inhibit the function of that compound by contacting it with the antibody or antibody fragment under conditions such that an immunocomplex forms inhibiting the function of the compound conjugated to the antibody or antibody fragment.

"Monoclonal antibodies" are substantially homogenous populations of antibodies to a particular antigen. They may be obtained by any technique that provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376,110.

"Polyclonal antibodies" are a group of heterogeneous antibodies produced by different B lymphocytes in response to the same antigen, wherein different antibodies in the group recognize different parts of the antigen.

Embodiments

One aspect of the present invention is a method of treating infertility in vivo using one or more neurotrophins to stimulate oocyte production and maturation, including the use of both paracrine and autocrine signaling pathways for different neurotrophins, which ultimately leads to increased fertility in female subjects. BDNF and NT-4/5 are both neurotrophins that bind to the Trk B receptor which is found on the surface of oocytes. Because of the location of the receptor for these neurotrophins, a therapeutically effective dose of the neurotrophin is preferably administered either directly to the oocyte or parenterally to another part of the subject so that the neurotrophin reaches the oocyte. BDNF and NT-4/5 preferably stimulate oocyte maturation via paracrite signaling, meaning that the neurotrophins are in contact with the object of their stimulation, namely, the Trk B receptors on the surface of the oocytes. NGF may also stimulate oocyte production via paracrine signaling by binding to Trk A receptors on the surface of oocytes.

In another embodiment, NT-3 also acts to stimulate oocyte maturation, but acts via an autocrine function. Preferably, NT-3 is administered to a female subject and is administered-in-a dose sufficient to aid the production of mature oocytes. NT-3 binds to Trk C receptors within the female nervous and reproductive system.

A therapeutically effective dose of a neurotrophin for administration in vivo is typically formulated with a pharmaceutically acceptable carrier, meaning one that is non-toxic to recipients at the dosages and concentrations employed and is compatible with other ingredients of the formulation. For example, the formulation would not contain any substances that are known to be deleterious to neurotrophins. The carrier may contain additives such as substances that enhance isotonicity and chemical stability. The additive materials may include buffers such as phosphate, citrate, succinate, acetic acid, and other organic acids or their salts; antioxidants such as ascorbic acid; low molecular weight (less than about twelve residues) polypeptides, proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, trehalose, glucose, mannose, or dextrins; chelating agents such as EDTA; sugar alcohols such as mannitol or sorbitol; counter-ions such as sodium; and/or nonionic surfactants such as polysorbates, poloxamers, or PEG. The final neurotrophin preparation maybe a liquid or lyophilized solid. The neurotrophin a suitable derivative or metabolite thereof may be used alone or in admixture with one or more additional active agents. More than one type of neurotrophin may be administered in the same composition. For example, both BDNF and NT-4/5 may be found in the same composition administered to a subject to treat infertility.

The neurotrophins and therapeutic compositions thereof discussed in the methods 20 of the present invention are also suitably administered by sustained-release systems, such as semi-permeable polymer matrices in the form of shaped articles, like microcapsules. Sustained-release matrices include polylactides, copolymers of L-glutamic acid and gamma-ethyl-L-glutamate, poly (2-hydroxyethyl methacrylate), ethylene vinyl acetate or poly-D-(–)-3-hydroxybutyric acid. Sustained release compositions also include liposomally entrapped compounds. The liposomes are preferably about 200-800 Angstroms unilamellar type.

Neurotrophins to be used for therapeutic administration are preferably sterile, and this may be achieved using filtration through sterile filtration membranes of about a 0.2 micron size. Therapeutic neurotrophin compositions generally are placed into a container having a sterile access port, for example, an intravenous solution bag or vial having a stopper pierceable by a hypodermic injection needle. The above formulations are also suitable for in vitro uses.

Neurotrophin ordinarily will be stored in unit or multi-dose containers, for example, sealed ampules or vials, as an aqueous solution, or as a lyophilized formulation for reconstitution. As an example of a lyophilized formulation, 10-mL vials are filled with 5 mL of sterile-filtered 1% (w/v) aqueous neurotrophin solution, and the resulting mixture is lyophilized.

The therapeutically effective dose of neurotrophin in the present invention will generally be in the range of about 0.01 µg/kg to about 100 mg/kg per day. Preferably, from 0.1 to 1 µg/kg. A clinician will administer neurotrophin formulations of the invention until a dosage is reached that improves the infertility condition, taking into account the usual factors of age, body weight, health, and other factors individual to the subject. The progress of this therapy is easily monitored by conventional assays.

An additional aspect of the invention is to improve the quality and fertility of oocytes. In this aspect of the invention, the oocytes may be improved either in vivo or ex vivo. In this aspect, the oocytes may be either immature or fully developed. This invention may be used human or non-human female animal subjects. If used on human subjects, the method is preferably used subjects who are infertile, who can not conceive without scientific intervention, or subjects who may not be able to conceive without scientific intervention in the future, such as subject preparing to undergo chemotherapy. If used on non-human subjects, the method is preferably used on animals in captivity and most preferably on endangered species.

The methods of the present embodiment first require removing the oocytes, preferably immature oocytes, from follicles in the ovary. This may be accomplished by conventional techniques, such as using the natural cycle or ovulation induction methods, during surgical intervention such as oophorerectomy, during hyperstimulation protocols in the context of an IVF program, or by necropsy. In the natural cycle, ultrasound or laparoscopy allows identification of one or more burgeoning follicles on the ovarian surface near midcycle. The follicles approaching ovulation are distended and substantially translucent. The follicles are then aspirated with a needle and one or more oocytes are extracted transvaginally. The oocytes are then evaluated based on the number and density of surrounding granulosa cells, the presence or absence of the first polar body, and the thickness of the zona pellucida, as well as other factors The invention also contemplates improving the fertility of already maturing oocytes including oocytes from hormone stimulated subjects, so that the oocytes are more mature than oocytes from unstimulated ovaries. Agents used to induce such controlled multiple follicular maturation include inhibin administered directly to the ovary, clomiphene citrate or human menopausal gonadotropins, or a mixture of FSH and LH, and/or human chorionic gonadotropins. These fertility agents are administered in therapeutically effective amounts. A gonadotropin releasing hormone agonist or antagonist may also be used in conjunction with FSH.

In this aspect after extraction, therapeutically effective doses of neurotrophins are administered to the oocyte. In the preferred embodiment, the neurotrophins are BDNF or NT-4/5 or a combination of both. The neurotrophins preferably bind to the Trk B or Trk A receptors on the oocyte and stimulate the growth and maturation of the oocyte, leading to a mature, healthy oocyte ready for fertilization. The neurotrophin to be administered will be either alone or preferably mixed with a pharmaceutical carrier. If the inventive method occurs in vivo, the subject will preferably produce one or more mature, healthy oocytes that are primed for fertilization. If the inventive method occurs in vitro, the oocyte will mature and will be fertilized with sperm at the appropriate time. When the resulting embryo reaches a 4-8 cell stage or as a blastocyst, it is preferably implanted the carrier and develop until birth.

Figure 3:
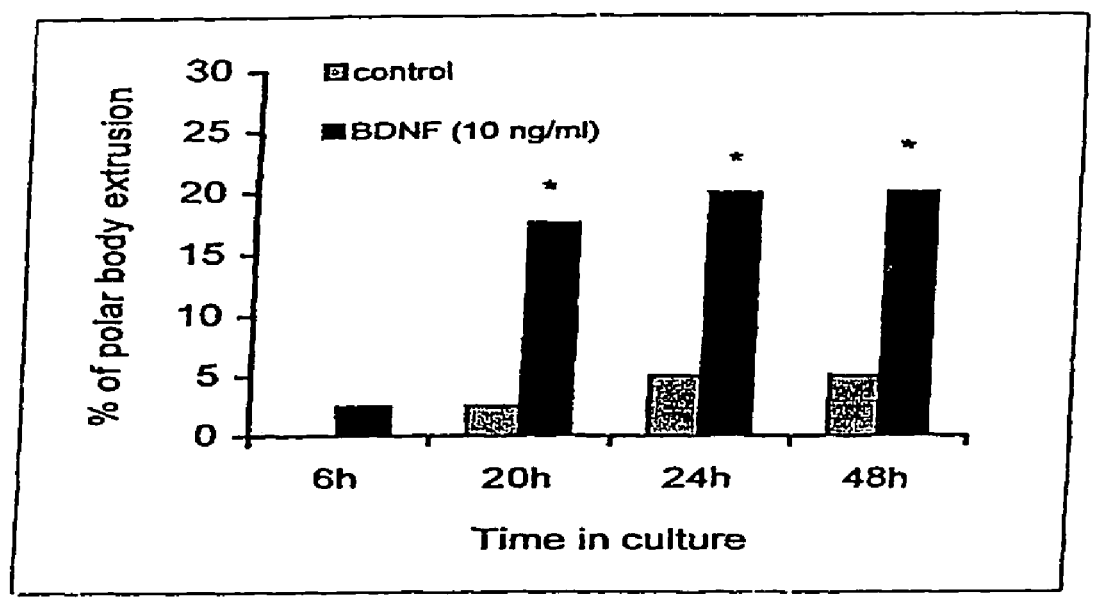
FIG. 3. BDNF influences upon mouse oocyte polar body extrusion. Forty oocytes from six mice (C57BL) were cultured in each of the control and study groups. *p<0.05
Figure 5:
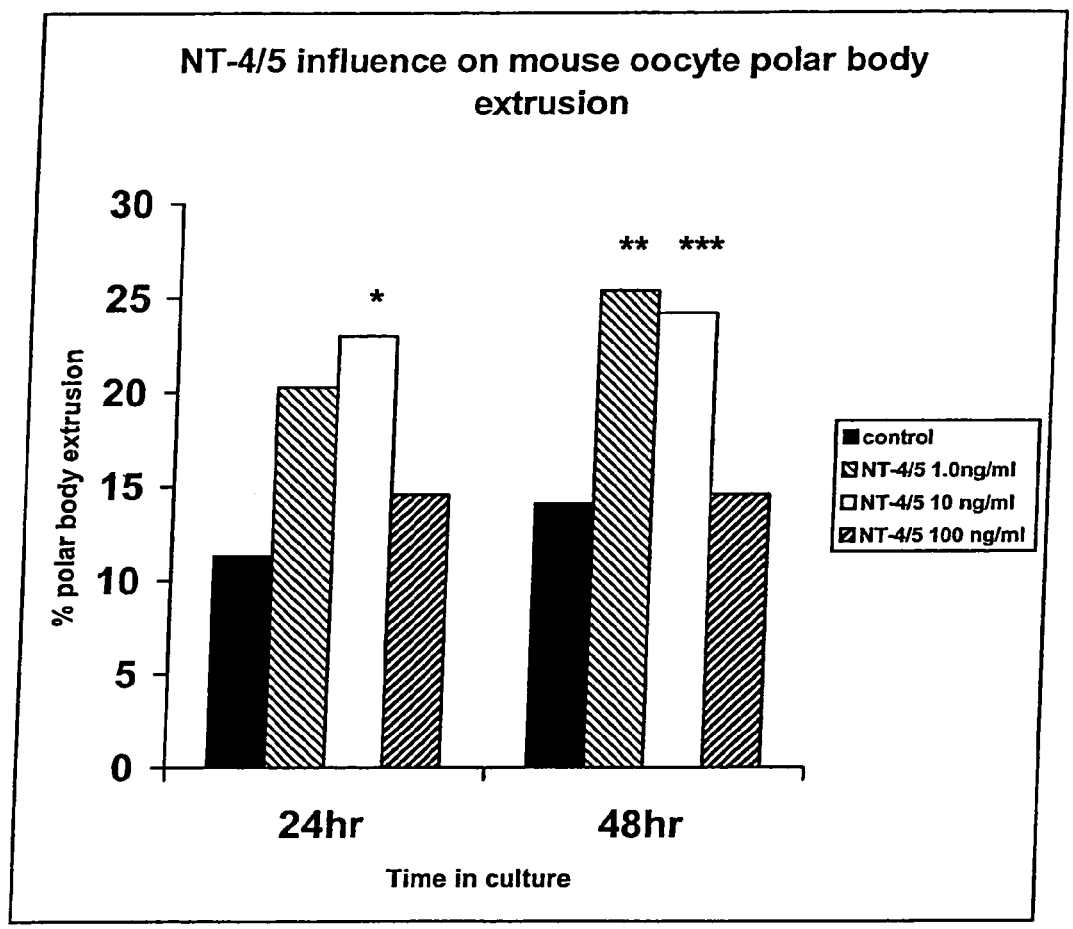
FIG. 5. Graph showing the influence of NT-4/5 on mouse oocyte polar body extrusion at 24 hours and 48 hours at concentrations of 1.0 ng/ml, 10 ng/ml, and 100 ng/ml.

In Example 3 of the present invention, first polar body extrusion was used as an indication of oocyte maturity and development when BDNF was administered. After six hours of exposure to 100 ng/ml of BDNF, first polar body extrusion was 18.8%; after 24 hours of exposure to 100 ng/ml of BDNF, first polar body extrusion was 20.0%; after 48 hours of exposure to 100 ng/ml of BDNF, first polar body extrusion was 21.3%. Control oocytes showed a much slower development rate. See FIG. 3. When NT-4/5 was administered to oocytes, NT-4/5 had an influence on mouse oocyte polar body extrusion at 24 hours and 48 hours at concentrations of 1.0 ng/ml, 10 ng/ml, and 100 ng/ml as shown in FIG. 5.

Figure 2A:
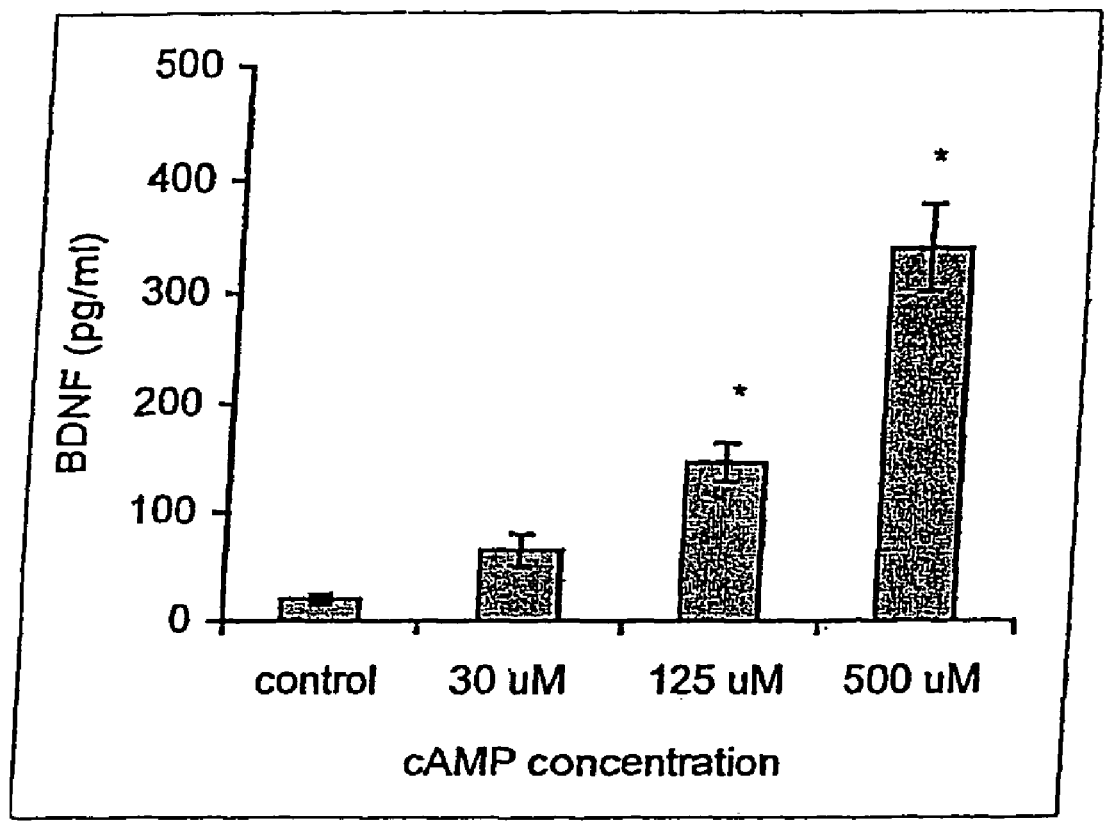
FIG. 2a. Effect of cAMP upon cumulus cell BDNF production and secretion. Cumulus cells were plated at $1.5 \times 10^5$ in 0.3 ml medium in 24-well plates. Cells were cultured for 24 h with treatment of 8-bromo-cAMP at concentration of 0 μM, 30 μM, 125 μM, and 500 μM. Graph was plotted using mean±SE. *p=0.02.
Figure 2B:
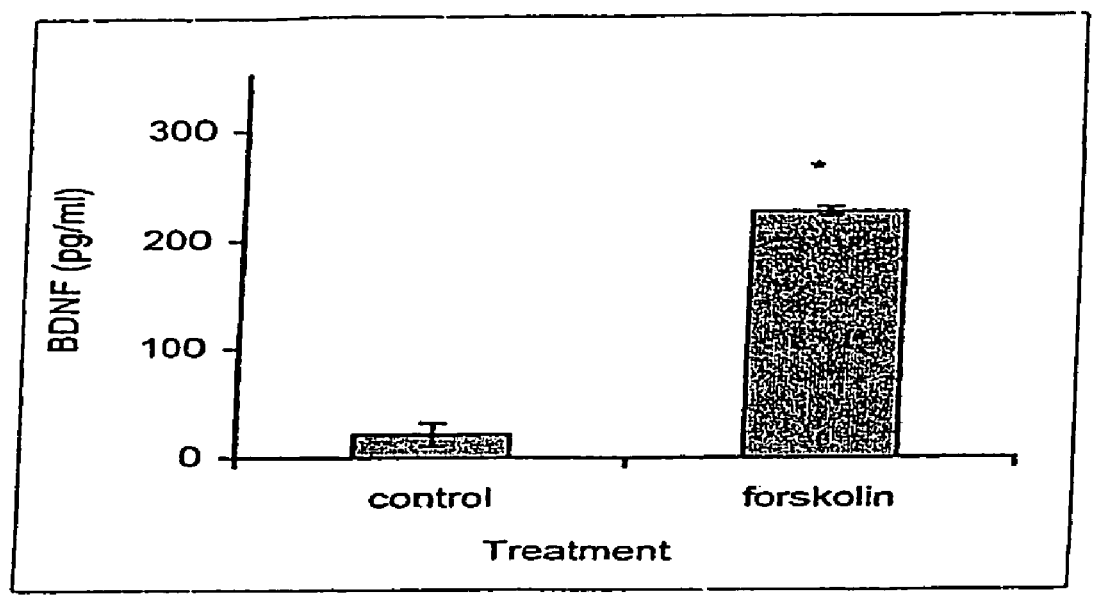
FIG. 2b. Effect of forskolin upon cumulus cell BDNF production and secretion. Cumulus cells were cultured for 24 h with or without 10 μM forskolin. Mean±SE. *p=0.016.

A third aspect of the present invention is the use of cAMP or cAMP analogues and related signal transduction factors, particularly forskolin, either alone or in combination to stimulate oocyte maturation. cAMP analogues may be used in about the 0.1-5 mM range when permeability is a factor because cAMP analogues are 3-4 times more permeable than normal cAMP. In the present invention in Example 1, 8-bromo-cAMP was administered at doses of 30 µM, 125 µM, and 500 µM. See FIG. 2a. Forskolin is preferably administered in the 1-100 µM range, more preferably 1-20 µM. See FIG. 2b.

Signal transduction agents that govern a cascade of processes by which an extracellular signal interacts with a receptor at the cell surface, causing a change in the level of a second messenger (cAMP in the present invention) and ultimately effects a change in the cells functioning. If the procedure involves in vitro oocyte maturation, cAMP and/or forskolin is preferably added to the developing oocyte cell solution. If the procedure involves in vivo oocyte maturation, cAMP and/or forskolin may either be in introduced to the oocyte through exogenous addition to the ovary or through stimulation of endogenous production in the subject's body such that the cAMP interacts with the oocyte. In a preferred embodiment, the combination of the second messenger, cAMP, with its signal transduction agent speeds the maturation of the oocyte even faster than application of either substance alone and further increases the potential fertility of the female subject. Finally, it is also contemplated that an exogenous neurotrophin, cAMP, and a signal transduction factor either be administered all at once or in succession to a female subject to speed oocyte maturation.

An additional aspect of the present invention is a method for stimulating oocyte maturation in vitro for IVF and other fertility procedures. As described above, any suitable procedure for extracting the oocyte from a female subject is acceptable as long as it protects both the subject and the integrity of the oocyte. Once extracted, any neurotrophin that exhibits a paracrine signaling pathway is preferred. Here, it is preferred that BDNF, NT-4/5 or NGF be administered to the oocyte, either individually or in combination with other neurotrophins. It is also preferred to add cAMP and/or any signal transduction factor in any combination found to stimulate oocyte maturation. This ultimately increases the potential of the oocyte for fertilization and reintroduction into a female subject for embryonic development.

Another aspect of the present invention includes the method of using neurotrophins to test female reproductive capability by extracting oocytes, adding a neurotrophin and then testing the amount of bound neurotrophin to the surface of one or more oocytes in a sample using either a test for the neurotrophin itself or using monoclonal antibodies that bind to the neurotrophin. Preferably, the neurotrophin is labeled to aid detection and quantification. More preferably, the neurotrophin is labeled with florescence or radioactive material by methods known in the art. A kit for carrying out the method is also provided. The presence and quantity of the neurotrophin is a positive prognosticator for reproductive capability and the absence of the neurotrophin is a negative prognosticator. In this aspect, the oocytes would be extracted as described above. Then, a neurotrophin of choice would be administered to the oocytes in vitro. Preferably, the neurotrophin would be either BDNF, NT-4/5, or NGF. After removing any unbound neurotrophin, in a first preferred embodiment, the amount of selected neurotrophin bound to at least one oocyte would be measured. If the neurotrophin were BDNF or NT-4/5, it would preferably be bound to the Trk B receptor, although it could be bound to another location on the oocyte. If the neurotrophin were NGF, it would preferably be bound to the Trk A receptor, although it could be bound to another location on the oocyte. The amount of neurotrophin bound to the oocyte would be measured because the amount of bound neurotrophin positively correlates to the reproductive capacity of the oocyte. The more receptors per oocyte that are present on the oocytes of a given subject, the greater the reproductive potential in that subject. The reason for this is that the more neurotrophin that can bind to the oocyte, the faster the oocyte will mature. Most preferably, a statistically significant sample of a number of oocytes from a given subject is tested to eliminate bias from testing one or a few number of oocytes. A kit for this embodiment may include the neurotrophin of choice. any necessary reagents for conducting the test, a label for the neurotrophin, and instructions for use.

The second preferred embodiment is very similar to the first for testing the number of receptors, preferably Trk B or Trk A receptors, on a sample of oocytes. The oocytes are extracted and placed in a suitable in vitro environment. Neurotrophins, preferably BDNF, NT-4/5, or NGF are added and the excess, unbound neurotrophins are removed. Then, monoclonal antibodies are added that have specific binding affinity to the neurotrophins already bound to the oocytes. The monoclonal antibodies are preferably labeled with florescence or radioactive material as known in the art. In this embodiment, the unbound monoclonal antibodies are again removed and the bound monoclonal antibodies are measured. Here, the quantity of monoclonal antibody bound to the oocyte is measured and the amount positively correlates to the reproductive capacity of the oocyte. A kit for this embodiment may include the neurotrophin of choice, the monoclonal antibody specific for the chosen neurotrophin, any necessary reagents for conducting the test, a label for the monoclonal antibodies, and instructions for use.

Another embodiment of the present invention teaches a method for screening Trk receptors on the surface of oocytes for genetic abnormalities, such as point mutations and gene rearrangements. In this embodiment, oocytes are extracted from a female subject using methods known in the art. As described herein and known in the art, the harvest of oocytes from human subjects typically includes receiving gonadotropin-releasing hormone (GnRH) agonist or antagonist to suppress ovulation, followed by human chorionic gonadotrophin (HCG) injection, and then oocyte retrieval. Once removed, the receptor of interest on the oocytes is extracted from the remainder of the oocyte and the receptor is sequenced using methods known in the art. The nucleic acid sequence of the receptor from the sample oocyte would then be compared against known normal, non-mutated nucleic acid receptor sequences for the same receptor. Preferably, the receptor on the oocyte would be the Trk B or Trk A receptor. Any genetic abnormality could be studied. In the present invention, it is preferred that point mutations, mutations that cause the replacement of a single base pair with another pair, and gene rearrangements, structural alterations of a chromosome that cause a change in the order of its loci, are studied.

In the present invention, a method and kit for measuring one or more endogenous neurotrophin levels in a female subject as a prognosticator of reproductive capacity are contemplated. In this aspect, bodily fluid would be extracted from a female subject. The bodily fluid is preferably follicular fluid or blood, but may also be urine, saliva, or any other bodily fluid containing neurotrophins. The bodily fluid would then be assayed for the concentration or level of at least one neurotrophin. Preferably, the neurotrophins examined in the assay would be BDNF, NGF, NT-4/5, or NT-3. Most preferably, the neurotrophins examined in the assay would be BDNF or NT-4/5. The higher the concentration of endogenous neurotrophins produced by the female subject, the greater the inherent reproductive potential, given that increased levels of neurotrophins positively correlate to reproductive potential. See FIG. 1. A kit for this aspect is also contemplated and would include the reagents and materials for testing endogenous neurotrophin levels and instructions for use.

A separate aspect of the invention contemplates testing the level of neurotrophins secreted by extracted cumulus cells in culture media to test the reproductive potential of female subjects. One or more cumulus cells are extracted by known methods as discussed above and placed in culture media. The culture media in which the cumulus cells are kept is preferably liquid and would allow for the growth, storage, transport, and maintenance of the cumulus cells. While the cumulus cells remain in culture media they preferably continue to carry out their normal functions including potentially secreting neurotrophins into their environment, which is the culture media. The culture media is then assayed for the concentration of one or more neurotrophins, preferably BDNF, NT-4/S, or NGF. The concentration based on the total number of cumulus cells in culture is then calculated. The higher the concentration of neurotrophins secreted by the cumulus cells, the greater the reproductive capacity of the female subject.

An additional aspect of the invention includes the use of antagonists to block the receptor sites for neurotrophins on oocytes and act as a contraceptive. An oocyte contains many types of receptors that bind ligands responsible for the growth and maturation of the oocyte. If an antagonist were bound to the receptor, it would interfere with the binding of the corresponding ligand and interfere with the action of that ligand. Preferably, the antagonist is bound to the Trk B receptor, blocking the binding of a neurotrophin, preferably BDNF or NT 4/5. The antagonist may also be bound to the Trk A receptor and block the binding of NGF. The antagonist could be any substance or drug that binds to the oocyte receptor, but is preferably an antibody. When the neurotrophin is unable to bind, it cannot act on the oocyte to allow its maturity and growth and would leave the oocyte immature. An immature oocyte is unable to be fertilized and thus, addition of antagonists to block neurotrophin receptors would act as a contraceptive in the female subject. The antagonist may be administered in any effective manner, but preferably orally or parenterally, and in any pharmaceutically effective dose. The administering clinician will determine the dose based on factors relevant to the individual subject.

EXAMPLES

The following experimental examples illustrate the efficacy of the inventive method, composition, and kit as described herein, test multiple neurotrophins, and provide both mice and human data. The examples are illustrative and should not be construed as limiting. Various changes and modifications obvious to one skilled in the art to which the present invention pertains are deemed to be within the spirit, scope and contemplation of the present invention as further defined in the appended claims.

BDNF Studies in IVF Subjects and Mice

In a series of experiments derived from human specimens from in vitro fertilization (IVF) following oocyte retrieval, BDNF was detected in human follicular fluid. To define the source of BDNF, cumulus granulosa cells, which are cells that immediately surround the developing oocyte, were grown in cell cultures for 1-2 days. BDNF protein increased over 24 hours in the culture medium. Moreover, the release of BDNF was enhanced upon stimulation with cyclic AMP (cAMP) and forskolin, an activator of cAMP. Cyclic AMP is a protein that activates protein kinases by binding regulating subunits resulting in phosphorylating target proteins in the cell.

In contrast, mural granulosa cells, which line the follicle, oocytes and embryos did not release appreciable quantities of BDNF. To examine possible targets of BDNF, mouse studies were used to localize immuno-cytochemically Trk-B, the BDNF receptor on oocytes. The receptor was present on the surface of isolated oocytes. Moreover, BDNF promoted oocyte maturation in culture. These experiments demonstrate for the first time the presence and secretion of BDNF from follicular cells and a role for BDNF in the regulation and modulation of oocyte maturation.

Therapeutic preparations of BDNF and BDNF antibodies of the invention include those utilizing pharmaceutically acceptable carriers, or other adjuvants as needed, and are prepared in effective dosage ranges as needed. The route of administration is one that allows the BDNF antibodies to reach the target cells. Appropriate dosage levels will depend on the subject and the therapeutic purpose.

Example 1

The regulation of BDNF by gonadotropin stimulation to improve the probability of pregnancy is demonstrated through the use of 8-bromo-cAMP (see FIG. 2$a$). 8-bromo-cAMP increased BDNF production and secretion by 3.3 fold at 30 µM, 7.4 fold at 125 µM (p=0.02) and 17.1 fold at 500 µM (p=0.0$^2$).

Example 2

The regulation of BDNF by activation of the gonadotropin production pathway to improve the probability of pregnancy is demonstrated through the use of forskolin. See FIG. 2$b$. Forskolin, an activator of intracellular adenylate cyclase to elevate intracellular cAMP, which increased BDNF production by 11 fold (P=0.016).

Example 3

The up-regulation of BDNF to improve the quality of oocytes for use in IVF and improve implantation rates and control the rate of meiosis. The percentage of oocytes demonstrating 1st polar body extrusion was higher after six (6) hours in the presence of 100 ng ml BDNF than in the control oocytes. Significantly higher rates of polar body extrusion in the presence of BDNF were seen at 20 hours (6.3% and 18.8%, p=0.017), 24 hours (6.3% and 20%, p=0.01) and 48 hours (7.5% and 21.3%, p=0.013) for control and treated oocytes, respectively. See FIG. 3.

Materials and Methods

Thirty-nine (39) women who were less than forty (40) years of age had follicular fluid containing granulosa cells aspirated while undergoing oocyte retrieval for in vitro fertilization (IVF). All had received leuprolide acetate (Lupron; Tap Pharmaceuticals, North Chicago, Ill.) for pituitary desensitization. After adequate suppression, two to eight ampules 150-600 IU of gonadotropins were given daily in divided doses between morning and evening. Transvaginal follicular aspiration was performed under sedation thirty-six (36) hours after HCG 10 (Human Chorionic Gonadotropin) injection. Pregnancy was defined as fetal cardiac activity on ultrasound performed four (4) weeks or more after follicular aspiration. Approval of this study was obtained from the IRB.

Follicular Fluid Collection

Follicular Fluid and granulosa cells were isolated by follicular aspiration of eighty (80) follicles from thirty-nine (39) women undergoing in vitro fertilization/embryo transfer. Clear follicular fluid without blood or flushing solution was obtained from one or more individual follicles measuring greater than 17 mm in diameter. Fluid was centrifuged at 1000 rpm for 10 minutes to remove the cellular component. The clear supernatant fraction was stored at $-80°$ C. for assay of BDNF.

Granulosa Cell Culture

Additional follicular aspirates were obtained and pooled within a subset of individual subjects (n=18) for the purpose of granulosa cell culture. The follicular fluid was centrifuged 10 minutes} 700×g at 20° C. The top layer of cells enriched with granulosa was carefully collected into Hanks balanced salt solution (HBSS, Ca and Mg-free). The cell suspension was carefully overlaid on top of 50% Percoll and centrifuged for 20 minutes at 700×g. Following Percoll separation, the granulosa cell enriched interface layer was collected and washed in HBSS. The resultant granulosa cell pellet was incubated in Hank's medium containing 2 mM EDTA for 5 minutes and vortexed at low speed. The granulosa cell suspension was further purified with anti-CD45 immunomagnetic beads (Beckman Coulter, Miami, Fla.) to remove residual lymphocytes from the cell suspension yielding a greater than ninety-five (95%) percent pure-sample as defined morphologically. Cumulus cells, which are a mass of epithelial cells surrounding the ovum in the ovarian follicle, were removed from oocytes in preparation for IVF and were dissociated in hyaluronidase (100 IU/ml, Sigma Chemical Company, St. Louis, Mo.) then washed twice with HBSS. The resulting preparation of cumulus cells was of ninety-nine percent (99%) pure.

Both mural (n=7) and cumulus (n=18) granulosa cells were plated at a density of 0.5 million cells per ml. Mural and cumulus cells were cultured in F-10 medium supplemented with ten (10%) percent (fetal bovine serum) FBS at 37° C., 5% $CO_2$. Culture media was collected at 24 and 48 hours and frozen at $-80°$ C. for assay of BDNF. For the purpose of examining the regulation of BDNF expression by cAMP, cumulus cells were combined between two subjects for each experiment. After 24 hours of initial culture, cells were rinsed three times and changed to fresh media with and without 8-bromo-cAMP (Sigma, St. Louis, Mo.) at concentrations of 30, 125 and 500 μM respectively and forskolin, an activator of cAMP, (10 M, Sigma, St. Louis, Mo.). The culture media was collected after 24 hours of culture for assay of BDNF. (See FIG. 1).

Human Oocyte and Embryo Culture-Medium

One hundred forty-seven (147) stripped (without cumulus) oocytes were obtained from ten (10) subjects. Oocytes were pooled within each subject and were incubated 3 to 5 hours at 37° C. 5% $CO_2$ in human tubal fluid (HTF) microdrops (40 l/drop) which were supplemented with 10% synthetic serum substitute (SSS) prior to intracytoplasmic sperm injection (ICSI). Following ICSI, oocytes were transferred to culture medium drops under oil and the HTF drops collected were frozen at −20° C. for BDNF assay. Seventy-six (76) zygotes resulted from ICSI and were cultured in Basal XI (Sage Biopharma, Bedminster, N.J.) with 10% SSS for 72 hours prior to embryo transfer. One to two zygotes were cultured in each 25 1 drop of culture media. The 72-hour embryo culture media was collected and frozen at −20° C. for BDNF assay.

BDNF Assay

BDNF levels were determined using commercially available BDNF E max® immumoassay system (Promega, Madison, Wis.). The ELISA's were performed according to the manufacture's protocol. Follicular fluid, granulosa cell culture media, oocyte or embryo culture media was added to a 96-well immunoplate pre-coated with human BDNF specific monoclonal antibody. The plate was incubated at room temperature for 2 hours with shaking. Anti-BDNF monoclonal antibody was used as the capture Ab and Anti-BDNF pAb was used as reporter Ab. After washing, the amount of specifically bound pAb was detected using a species-specific anti-IgY antibody conjugated to horseradish peroxidase (HRP) as a tertiary reactant. The unbound conjugate was removed by washing followed by incubation with a chromogenic (color-generating) substrate. A chromogenic substrate is colorless until acted upon by an enzyme; it then becomes an insoluble pigment. Absorbency was measured at 450 nm using a microplate reader (Model Vmax kinetic microplate reader; Molecular Devices). All samples were assayed in duplicate. The BDNF antibody demonstrated less than 3% cross reactivity with other related neurotrophic factors (NGF, NT-3 and NT-4/5) at 100 g/ml. The detection sensitivity of the ELISA was 15.6 pg/ml with an intrassay coefficient of variation of 2.2% at a mean concentration of 286.1 pg/ml BDNF, according to the manufacturer. The interassay coefficient of variation of the ELISA assay was 8.6%.

Several negative control experiments were performed to rule out nonspecific binding to human BDNF antibody and potential human IgG from serum contamination that could theoretically crossreact with the ELISA assay. Negative controls included: (1) absence of the reporting antibody specific to BDNF and (2) absence of the reporting antibody and the ligand. These negative controls were included in each assay performed and demonstrated the absence of nonspecific binding.

Example 4

The activation of the Trk B receptor on unfertilized, pre-ovulatory oocytes that results in an up-regulation of BDNF and maturation of oocytes. Seventy-five (75) oocytes (43 exposed to anti-Trk B antibody, 32 controls) from five mice were successfully evaluated in three experiments.

Three types of stain reaction were observed: 1) intense, almost black stain within 10-20 seconds of DAB addition (diaminobenzidine tetrahydrochloride), indicative of a positive reaction; 2) light pink color appearing over the course of 3-5 minutes (equivocal staining); or 3) no discernible color change after greater than 5 minutes (negative reaction). Thirty-six (36) oocytes (84%) exposed to anti-Trk B antibody demonstrated intense, positive staining while 7 oocytes (15%) demonstrated equivocal or negative staining. None of the control oocytes exhibited a positive staining reaction. Twenty-two (22%) percent of the control oocytes exhibited equivocal staining while 78% of controls demonstrated no-color change. The proportion of oocytes stained was significantly greater in the group exposed to anti-Trk B than in controls not exposed to anti-Trk B antibody ($p<0.0001$).

Trk B Receptor Identification in Mouse Oocytes

Mice (C57BL/6 mice, Taconic Labs), 4-5 weeks old, were injected intraperitoneally with 6-8 IU pregnant mare serum gonadotropin (PMSG, Sigma Chemical Company, St. Louis, Mo.). Forty-eight (48) hours later, mice were euthanized with $CO_2$ and ovaries were removed and placed in ice-cold peripheral blood serum (PBS) (0-2° C.). Oocytes were isolated using 27 gauge needles under the stereoscope. Isolated oocytes were pooled into cold PBS until dissection was completed. Isolated oocytes were transferred into ELISA wells (Removalwell, Dynex Tech, Incorporated, Chantilla, Va.) or 4-well Nunc (Nunculon 176740, Nalge Nunc International, Rochester, N.Y.) chambers in PBS. After replacing the PBS with 4% paraformaldehyde, wells were sealed with parafilm and stored overnight at 4-8° C. After paraformaldehyde fixation, oocytes were washed three times with cold PBS and stored in PBS at 4-8° C. until stained.

For Trk B receptor staining, PBS was replaced with 15% goat serum in 0.3% TritonX buffer (Sigma Labs) for 30-60 minutes at room temperature. Oocytes were then washed three times with PBS at room temperature, followed by overnight incubation at 4-8° C. in 1:200 rabbit anti-Trk B antibody that recognizes an intracellular domain of intact Trk B receptor. Following incubation with Trk B antibody oocytes were rinsed three times with PBS then incubated one (1) hour at room temperature in goat anti-rabbit IgG (1:200) (Vector Labs). Oocytes were again rinsed three times with PBS and incubated one (1) hour in avidin-biotinylated enzyme complex (ABC reagent, Vectastain® Elite, Vector Labs) followed by three (3) rinses with tris-buffer. The final tris-buffer was replaced-with diaminobenzidine tetrahydrochloride (DAB) (Vector Labs) under stereoscopic visualization recording the time required for oocyte staining to occur. Control oocytes were treated as above except that rabbit anti-Trk B antiserum was omitted.

Effect of BDNF upon in Vitro Maturation of Mouse Oocytes

Six (6) 4-5 week old female C57BL/6 mice (Taconic Labs, German Town, N.Y.) were given a single intraperitoneal injection of 7.5 IV PMSG (Sigma, St. Louis, Mo.). One hundred sixty (160) immature oocytes were harvested 48 hours after gonadotropin injection. Cumulus cells were removed mechanically (27 gauge insulin needles) at room temperature. Oocytes were equally divided into control and experimental groups. Immature oocytes (n-80) were incubated (5% $CO_2$ in air, 37° C.) in Human Tubal Fluid (HTF, Conception Technologies, San Diego, Calif.) with 100 ng/ml BDNF (Peprotech, Inc. Rocky Hill, N.J.) Control oocytes (n=80) were cultured in HTF under the same conditions without addition of BDNF. The percentage of oocytes demonstrating germinal vesicle breakdown (CVBD) and/or 1st polar body extrusion was recorded after 1, 2, 3, 6, 24 and 48 hours in culture. (See FIG. 3).

Statistical Analysis

Statistical analysis of data was performed using an unequal variance two-tail t-test. Fisher's exact test or Chi-square for group comparisons where appropriate.

BDNF Studies in Normal Cycling Subjects

Figure 4:
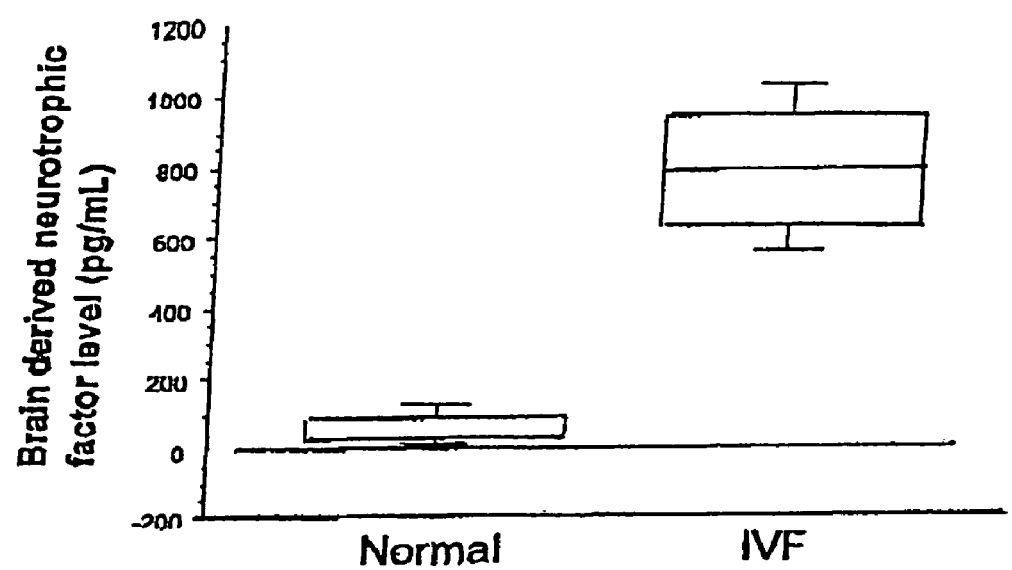
FIG. 4. Box and whiskers plot showing the range of BDNF levels in induced-ovulation subjects as compared to normal cycling subjects. The horizontal line in the center of the box shows the median value; the upper and lower limits of the box show the interquartile range; and the whiskers show the minimum and maximum values for each group.

The results of the first invention were confirmed through studying the presence of BDNF in the follicular fluid of preovulatory follicles in non-IVF, non-gonadotrophin, and non-hCG treated subjects. The study addressed the issue of whether BDNF is secreted within the context of normal ovarian physiology exclusively within the context of supraphysiologic pharmacologic doses of exogenous gonadotropins. Prior to this experiment, the assay for BDNF had been validated only for urine samples, not follicular fluid. (Promega Technical Bulletin #257 (1998)). The present study using "normal cycling subjects" proves that the presence of BDNF is not attributable to the treatments given to the first group of subjects, but that IVF does increase the levels of BDNF found. See FIG. 4.

Experiment 5

Ten normal cycling women with a history a regular menstrual cycles of 26-32 days comprised the study population. One follicular fluid sample from a single dominant follicle from each of these 10 women had been frozen at −80° C. and analyzed for inhibin/activin and follistatin. Subjects had taken no medication for three months prior to the aspiration of their dominant follicle. Pelvic ultrasonography was performed in the follicular (mean diameter$\geq$15 mm, range diameter 15-23 mm) was accompanied after the largest follicle from among the cohort of antral follicles was determined.

Follicular fluid from twenty age-matched women undergoing ovulation induction 20 for IVF with either male factor infertility or who were oocyte donors were chosen as a comparison group. Aspiration of follicles occurred with a mean diameter$\geq$17 mm, range diameter 17-24 mm, 36 hours after hCG injection. Follicular fluid samples had been frozen at 80° C.

BDNF levels were determined using the commercially available BDNF Emax immunoassay system (Promega Corp., Madison, Wis.). The ELISAs were performed according to the manufacturer's protocol. To validate the BDNF assay for follicular fluid; serial dilutions of three follicular fluid samples were checked for linearity and recovery of two doses of exogenous BDNF was assessed in IVF follicular fluid. Statistical analysis of data was prepared using a non-parametric Mann Withney U for group comparisons.

Subject groups were matched for age, with a mean age of 32.5±6.6 years in the normal cycle subjects and 33.0±5.2 years in the IVF subject group. BDNF was noted to be present in all follicular fluid samples, except for two normal follicles in which BDNF levels were at the limit of sensitivity of the assay. A 27-fold difference in BDNF follicular fluid concentrations was noted between normally cycling women and women undergoing ovulation induction in preparation for IVF. See FIG. 4. Median (interquartile range) BDNF levels in follicular fluid were 28.8 pg/mL (61.9 pg/mL) in normally cycling women and 780.0 pg/mL (314.9 pg/mL) in women undergoing ovulation induction in preparation for IVF ($P<0.0001$). Follicular fluid BDNF concentrations did not vary as a function of follicle size in normal follicles. The BDNF assay was valid for human follicular fluid measurement as demonstrated by the linear dilution of three IVF fluid samples. In addition, mean recovery of BDNF in follicular fluid was 89% at 125 pg/ml and 91% at 62.5 pg/ml.

This test confirms that BDNF is present in the follicular fluid of normally cycling 20 women and indicates that BDNF is a physiologic regulator of normal follicle maturation, but that BDNF levels are upregulated in the follicular fluid of women undergoing ovulation induction as compared to normally cycling women. BDNF levels were on average, twenty-seven times higher in follicular fluid from women undergoing ovulation induction and receiving hCG. This finding is consistent with the fact that exogenous gonadotropins increase cAMP which in turn leads to greater cumulus cell secretion of BDNF into the follicular fluid. This experiment validates the manipulation of neurotrophin binding on oocytes for both IVF and non-IVF subjects, proving that the invention has wide applicability.

NT-4/5 and NT-3 Studies in IVF Subjects and Mice

A second set of experiments was conducted to further test the effect of different neurotrophins on oocyte development to validate the use of neurotrophins on oocyte development as taught herein. Human follicular fluid and mouse immature oocytes were examined to determine whether another Trk B ligand, neurotrophin-4/5 (NT-4/5), is present with the ovarian follicle and if, so if it demonstrates activity similar to that of BDNF. Neurotrophin-3 (NT-3) was also tested to determine whether a non-Trk B neurotrophin ligand is present within the ovarian follicle and what its potential roles in oocyte maturation are.

Human Studies

Population

For this study, twenty women less than forty years old (mean±SE 36.7±0.6 years) had follicular fluid containing granulosa cells aspirated while undergoing oocyte retrieval for in vitro fertilization (IVF). All women took leuprolide acetate (Leupron; Tap Pharmaceuticals, North Chicago, Ill.) for pituitary desensitization. After adequate suppression, two to eight ampules of gonadotropins were given daily in divided doses between morning and evening. Transvaginal follicular aspiration was performed under sedation thirty-six hours after human chorionic gonadotropin (hCG) injection.

Follicular Fluid Collection Study

Follicular fluid and granulosa cells were isolated by aspiration of twenty three follicles from twenty women undergoing in vitro fertilization and embryo transfer. Clear follicular fluid without blood or flushing solution was obtained from one or more individual follicles measuring greater than 17 mm in diameter. Fluid was centrifuged at 1000 rpm for 10 minutes to remove the cellular component. The clear supernatant fraction was stored at −80° C. for assay of NT-4/5 and NT-3.

Assays

NT-4/5 and NT-3 were determined using the commercially available NT-4/5 Emax and NT-3 Emax immunoassay systems (Promega, Madison, Wis.). The ELISA's were performed according to the manufacturer's protocol Follicular fluid was added to a 96-well immunoplate pre-coated with human NT-4/5 or NT-3 specific polyclonal antibodies. Plates were incubated at room temperature for six hours with shaking. Anti-human-NT-4/5 or anti-human NT-3 monoclonal antibody (reporter antibody) was used. After washing, the amount of specifically bound reporter antibody (pAb) was detected using a species-specific anti-mouse IgG antibody conjugated to horseradish peroxidase (HRP) as a tertiary reactant. Unbound conjugate was removed by washing, followed by incubation with chromogenic substrate. Absorbency was measured at 450 nm using a microplate reader (Model Vmax kinetic microplate reader, Molecular Devices). All samples were assayed in duplicate.

Anti NT-4/5 was antibody crossreactive with related neurotrophin factors (BDNF, NGF, and NT-3) was reported to be less than 3% at 100 ng/ml. The detection sensitivity of the NT-4/5 ELISA was reported to be 9.4 pg/ml NT-4/5, according to the manufacturer. The interassay coefficient of variation for the NT-4/5 ELISA (enzyme linked immunosorbent assay) assay was 5:1%.

Anti NT-3 was reported by the manufacturer to demonstrate less than 3% crossreactivity with other related neurotrophin factors. The detection of the ELISA is 10 pg/ml with an intrassay coefficient of variation of 1.5% at a mean concentration of 227.0 pg/ml NT-3, according to the manufacturer. The interassay coefficient of variation in our ELISA was 6.2%.

Several negative controls were included in each assay to rule out nonspecific binding of anti-human NT-4/5, NT-3 antibody, or anti IgY binding to human serum IgG. Negative controls included (1) omitting NT-4/5 or NT-3 during initial reaction with immobilized antibody, (2) absence of antibody specific to NT-4/5 or NT-3 and (3) absence of the reporting antibody. These negative controls were included in each assay performed to demonstrate the 10 absence of nonspecific binding.

Mouse Studies

Effect of NT-4/5 and NT-3 on in Vitro Maturation of Mouse Oocytes

Eighteen 4-5 week old female C57BL/6 mice (Taconic Labs, German Town, N.Y.) were given a single intraperitoneal injection of 7.5 IU PMSG (Sigma, St. Louis, Mo.). Five hundred thirty-six (536) immature oocytes were harvested 48 hours after gonadotropin injection. Cumulus cells were removed mechanically (27 gauge insulin needles) at room temperature. Immature oocytes were equally divided into control (n=218) and experimental (n=318) groups and cultured in 5% $CO_2$ in air, 37° C. in Human Tubal Fluid (HTF, Conception Technologies, San Diego, Calif.) for 24 and 48 hours with 1 ng/ml (n=59), 10 ng/ml (n=98) and 100 ng/ml (n=11) of 10 NT-4/5 (Peprotech, Inc. Rocky Hill, N.J.) or 10 ng/ml (n=60) and 100 ng/ml (n=60) of NT-3 (Peprotech, Inc. Rocky Hill, N.J.) to examine the percentage of germinal vesicle breakdown. The percentage of polar body extrusion was also examined. Control oocytes (n=218) were cultured in HTF under the same conditions without addition of NT-4/5 (n=158) or NT-3 (n=60). The percentage of oocytes in a cohort of oocytes that demonstrated germinal vesicle breakdown (CVBD) and/or 1st polar body extrusion was recorded 24 and 48 hours in culture.

Trk C Receptor Identification in Mouse Oocytes

Six mice (C57BL/6 mice, Taconic Labs), 4-5 weeks old, were injected intraperitoneally with 6-8 IU pregnant mare serum gonadotropin (PMSG, Sigma Chemical Co., St. Louis, Mo.). Forty-eight hours later, mice were euthanized with $CO_2$ and ovaries were removed and placed in ice-cold PBS. Oocytes were isolated using 27 gauge needles under the stereoscope. Isolated oocytes were pooled into cold PBS until dissection was completed. Pooled oocytes were transferred into 4-well Nunc (Nunculon 176740, Nalge Nunc International, Rochester, N.Y.) chambers in PBS. After replacing the PBS with 4% paraformaldehyde, wells were sealed with parafilm and stored overnight in 4-8° C. Following fixation,) oocytes were washed three times with cold PBS and stored in PBS at 4-8° C. until stained.

Mouse oocyte Trk C receptor staining was carried out at room temperature. In brief, oocytes (n=152) were treated with blocking serum (15% goat serum with 0.1% Triton-X). Anti-Trk C treated oocytes (n=68) were then incubated 30-60 minutes at room temperature in 1:200 rabbit anti-Trk C antibody (sc-117, Santa Cruz Biotechnology, Inc., Santa Cruz, Calif.) directed against a peptide mapping near the carboxy terminus of Trk C gp 140. Following incubation with Trk C antibody, oocytes were incubated one hour at room temperature in goat anti-rabbit IgG (1:200) and then for 30-60 minutes in avidin-biotinylated enzyme complex (ABC reagent, Vectastain ® Elite, Vector Labs). Between each oocyte treatment, oocytes were rinsed three times in PBS. The final buffer was replaced with diaminobenzidine tetrahydrochloride (DAB) under stereoscopic visualization, with stain intensity recorded 10 minutes after the addition of DAB. Control oocytes (n=84) were treated as above except that the rabbit anti-Trk C antiserum was omitted or anti Trk C antibody was pre-absorbed with Trk C peptide mimicking the receptor peptide sequence against which the antibody was directed. Positive controls consisted of sympathetic ganglia dissected from day-old rat pups, fixed 2 hr in 4% paraformaldehyde, then equilibrated in 30% sucrose prior to cryostat sectioning and mounting on glass slides. Ganglia were incubated with either anti-Trk C (1:200) antiserum for anti-Trk C antiserum absorbed with blocking peptide (sc-117, Santa Cruz Biotechnology, Inc., Santa Cruz, Calif.).

Statistical Analysis

Statistical analysis of data was performed using an unequal variance two-tail t-test, Fisher's exact test or Chi-square for group comparisons where appropriate. Statistical significance was assumed at $p<0.05$.

Results

NT-4/5 and NT-3 were noted to be present in all human follicular fluid samples aspirated from follicles of women undergoing in vitro fertilization. The mean±SE follicular fluid concentrations of NT-4/5 and NT-3 were 397.0±71 pg/ml and 509.0±97 pg/ml, respectively. NT-4/5, but not NT-3, significantly promoted mouse oocyte polar body extrusion. NT-4/5 significantly influenced mouse oocyte polar body extrusion at 24 hours with 10 ng/ml (<0.01) and at 48 hours with 1.0 ng/ml ($p<0.05$) and 10 ng/ml ($p<0.01$). See FIG. 5. NT-4/5 did not influence germinal vesicle breakdown.

NT-3 did not alter the dynamics of mouse oocyte germinal vesicle breakdown or polar body extrusion compared to controls. While previous studies have indicated that Trk B receptors are present on oocytes, Trk C receptors were not noted to be present in mouse oocytes. There was no difference in the proportion of oocytes stained by anti-Trk C in the presence or absence of blocking peptide. Rat sympathetic ganglion sections demonstrated positive anti-Trk C staining which was completely blocked by pre-adsorption with blocking peptide.

These experiments demonstrate that NT-4/5 and NT-3 are present in the follicular fluid of the human ovary. The data suggests that NT-4/5, like BDNF, promotes oocyte nuclear maturation. The presence of Trk B in mouse oocytes, as discussed above, and in human fetal oocytes (Anderson et al. 2002), coupled with the finding of NT-4/5 in human follicular fluid and the demonstration that NT-4/5, like BDNF, promotes mouse oocyte MI polar extrusion suggests paracrine roles for both BDNF and NT-4/5 within the human follicle. The presence of Trk C in human granulosa cells (Shibayama 1996) and the presence of NT-3 in human follicular fluid, along with the absence of Trk C in mouse oocytes indicate an autocrine role for NT-3 in the human ovarian follicle. Together, these data support the concept that the presence of a family of neurotrophins (both Trk B and Trk C ligands) within the human ovarian follicle influence intrafollicular signaling pathways for communication between somatic cells (granulosa-granulosa) as well as between somatic and germ cells (granulosa-oocyte).

In contrast, the experiments did not show an effect of NT-3 on mouse oocyte GVBD or polar body extrusion which is consistent with the absence of Trk C receptors in the mouse oocyte. At the same time, NT-4/5, a Trk B ligand, significantly accelerated polar body extrusion relative to control oocytes not exposed to neurotrophin. Although NT-3 has been reported to bind to Trk B receptors, such a result was not observed in the present experiment. NT-3 may contribute to follicle and oocyte maturation, however.

References Cited

Anderson R A, Robinson Lynne L L, Brooks J, Spears N, 2002. Neurotropins and their family in human non-neuronal tissues. J Clin Endocrinol Metab 87:890-897.

Conover et al., 1995. Neuronal deficits, not involving motor neurons, in mice lacking BDNF and/or NT4. Nature, Vol. 375:235-238.

Dissen, G. A., Hill, D. F., Costa, M. E., Dees, W. L., Lara, H. F. and Ojeda, S. R., 1996. A role for Trk A nerve growth factor receptors in mammalian ovulation. Endocrinology. 137:198-209.

Dissen, G. A., Mayerhofer, A., Ojeda, S. R. 1998. Participation of nerve growth factor in the regulation of ovarian function. Zygote. 4:309-3 12.

Dissen, G. A., Hirshfield, A X, Malamed, S and Ojeda, S. R. 1995. Expression of neurotrophins and their receptors in the mammalian ovary is developmentally regulated: changes at the time of folliculogenesis. Endocrinology. 136:4681-4692.

Dissen, et al., 2000. Direct effects of nerve growth factor on the thecal cells from antral ovarian follicles. Endocrinology, 141:4736-4750.

Giudice, et al. 1996. Growth Factors in Normal Ovarian Follicle Development. Semin. Reprod. Endocrinol., 14:179-196.

Lara, H E., Hill, D. F., Katz, K. H. and Ojeda, S. R. 1990 The gene encoding nerve growth factor is expressed in the immature rat ovary: effect of denervation and hormonal treatment. Endocrinology. 126:357-363.

Lam, H E., McDonald J. K. and Ojeda, S. R. 1990 Involvement of nerve growth factor in female sexual development. Endocrinology. 126:364-375.

Mayerhoffer, A., Dissen, G. A., Parrot, J. A., Hill, D. F., Mayerhoffer, D., Garfield, R. E., Costa, M. E., Skinner, M. K. and Ojeda, S. R. 1996. Involvement of nerve growth factor in the ovulatory cascade: Trk A receptor activation inhibits gap junctional communication between thecal cells. Endocrinology. 137:5662-5670.

Mischel et al, 2001. The extracellular domain of p75NTR is necessary to inhibit neurotrophin-3 signaling through Trk A. J. Biol. Chem. 276:11294-11301.

Ojeda, S. R. Romero, C., Tapia, V. and Dissen, G. A. 2000. Neurotrophic and cell-cell dependent control of early follicular development. Mol Cell Endo. 163:67-71.

Parvinen et al., 1992. Expression of B-nerve growth factor and its receptor in rat seminiferous epithelium: specific function at the onset meiosis. J Cell Biol. 117:629-641.

Promega Technical Bulletin #257, 1998. BDNF $E_{max}$™ ImmunoAssay System.

Reichardt, L F, Farifias, I, 1997. In Molecular Approaches to Neural Development, Cowan M W, Jessell T M, Zipursky F L, eds. pp. 220-263 Oxford University Press, New York.

Schneyer, et al. 2000. Dynamic changes in the intrafollicular inhibin/activin/follistatin axis during human follicular development: relationship to circulating hormone concentrations. J. Clin. Endocrinol Metab. 85:33 19-3330.

Seidi et al. 1996. Expression of nerve growth factor and neurotrophin receptors in testicular cells suggest novel roles for neurotrophins outside the nervous system, Reprod. Fert. Dev., 8:1075-1087.

Seifer, D B, Feng B, Shelden R M, Chen 5, Dreyfus C F, 2002. Brain-derived neurotrophic factor: A novel human ovarian follicular protein. J Clin Endocrinol Metab 87:655-659.

Seifer D B, Gardiner A C, Lambert-Messerlain G, Schneyer A L 1996. Differential secretion of dimeric inhibin in cultured luteinized granulosa cells as a function of ovarian reserve. J Clin Endocrinol Metab 81:736-739.

Shibayama E, Koizumi H, 1996. Cellular localization of the Trk neurotrophin receptor family in human non-neuronal tissues. Am J Path 148:1807-1818.

Sommerfeld et al., 2000. Down regulation of the neurotrophin receptor TrkB following ligand binding, J. Biol. Chem., Vol. 275:8982-8990.

Tessarollo, L. 1998 Pleiotropic functions of neurotrophins in development. Cytokine and Growth Factor Reviews. 9:125-137.

Vesa et al., 2000. p75 Reduces Trk B tyrosine autophosphorylation in response to brain-derived neurotrophic factor and neurotrophin 4/5," J. Biol. Chem., 275:24414-24420

Waraksa, J. A., Lindsay, R. M., Ip N Y and Hutz, R. J. 1995. Neurotrophin-3 augments steroid secretion by hamster ovarian follicles in vitro. Zoolog Sci. 12:499-502.

Yamamoto, M., Sobue, G., Yamamoto, K., Terao, S. and Mitsuma, T. 1996 Expression of mRNAs for neurotrophic factors (NGF, BDNF, NT-3 and CDNF) and-their receptors $p^{75NPFR}$, Trk A, Trk B and Trk C) in the adult human peripheral nervous system and nonneural tissues Neurochemical Research. 21:929-938.

Zaccaro et al., 2001. p75 co-receptors regulate ligand-dependent and ligand-independent Trk receptor activation, in part by altering Trk docking subdomains. J Biol. Chem. 276:3 1023-31029.

We claim:

1. A method of stimulating oocyte maturation in an oocyte of a female subject, comprising administering brain-derived neurotrophic factor in its native sequence to at least one oocyte of said female subject, wherein the stimulation of oocyte maturation alleviates an infertility condition.

2. The method of claim 1, wherein brain-derived neurotrophic factor in its native sequence is administered, and wherein said brain-derived neurotrophic factor is administered in combination with neurotrophin-4/5 in its native sequence, or nerve growth factor in its native sequence.

3. The method of claim 1, wherein the stimulation of oocyte maturation occurs via a paracrine signaling pathway.

4. The method of claim 1, wherein the neurotrophin is combined with a pharmaceutically-acceptable carrier.

5. The method of claim 1, wherein the brain-derived neurotrophic factor (BDNF) is administered parenterally.

6. A method of effecting oocyte maturation, comprising:
administering brain-derived neurotrophic factor in its native sequence in a media to at least one harvested oocyte wherein the brain-derived neurotrophic factor binds to a receptor on the oocyte and stimulates oocyte maturation.

* * * * *